(12) United States Patent
Lagos-Quintana et al.

(10) Patent No.: US 9,179,654 B2
(45) Date of Patent: Nov. 10, 2015

(54) INHIBITION OF ANGIOGENESIS

(75) Inventors: Mariana Lagos-Quintana, Berlin (DE); Shahin Rafii, New York, NY (US); Sai H. Chavala, Durham, NC (US)

(73) Assignee: CORNELL RESEARCH FOUNDATION, INC., Ithaca, NY (US)

( * ) Notice: Subject to any disclaimer, the term of this patent is extended or adjusted under 35 U.S.C. 154(b) by 491 days.

(21) Appl. No.: 12/936,732

(22) PCT Filed: Apr. 7, 2009

(86) PCT No.: PCT/US2009/039808
§ 371 (c)(1),
(2), (4) Date: Feb. 1, 2011

(87) PCT Pub. No.: WO2009/126650
PCT Pub. Date: Oct. 15, 2009

(65) Prior Publication Data
US 2011/0184043 A1 Jul. 28, 2011

Related U.S. Application Data

(60) Provisional application No. 61/042,936, filed on Apr. 7, 2008.

(51) Int. Cl.
*A61K 48/00* (2006.01)
*C07H 21/02* (2006.01)
*C07H 21/04* (2006.01)
*A01K 67/027* (2006.01)
*C12N 15/113* (2010.01)

(52) U.S. Cl.
CPC ............ *A01K 67/027* (2013.01); *C12N 15/113* (2013.01); *C12N 15/1136* (2013.01); *A01K 2207/35* (2013.01); *A01K 2227/105* (2013.01); *A01K 2267/03* (2013.01); *C12N 2310/113* (2013.01); *C12N 2310/321* (2013.01); *C12N 2310/3233* (2013.01); *C12N 2310/3515* (2013.01)

(58) Field of Classification Search
USPC ........................................... 514/44; 536/24.5
See application file for complete search history.

(56) References Cited

U.S. PATENT DOCUMENTS

2005/0059005 A1    3/2005  Tuschl et al.
2005/0261218 A1   11/2005  Esau et al.
2008/0050744 A1    2/2008  Brown et al.

OTHER PUBLICATIONS

Musiyenko, A. et al. "Ectopic expression of miR-126, an intronic product of the vascular endothelial EGF-like 7 gene, regulates prostein translation and invasiveness of prostate cancer LNCaP cells," J. Mol. Med. (2008) 86:313-322.
Tavazoie, S.F. et al., "Endogenous human microRNAs that suppress breast cancer metastasis," Nature, vol. 451, Jan. 10, 2008, pp. 147-152.
Kulshreshtha, R. et al., "A microRNA component of the hypoxic response," Cell Death and Differentiation (2008) 15, 667-671.
International Search Report and Written Opinion for corresponding International Patent Application No. PCT/US2009/039808.
Wang S. et al., "The Endothelial-Specific MicroRNA miR-126 Governs Vascular Integrity and Angiogenesis", Developmental Cell 15:261-271 (Aug. 12, 2008).

*Primary Examiner* — Terra C Gibbs
(74) *Attorney, Agent, or Firm* — Scully, Scott, Murphy & Presser, P.C.

(57) ABSTRACT

The present invention relates to the microRNA miR-126 and to inhibitors of miR-126 that regulate angiogenesis. The present invention provides compositions and methods for the inhibition of miR-126 and for the inhibition of angiogenesis in vivo.

23 Claims, 6 Drawing Sheets

Figure 4A
Figure 4
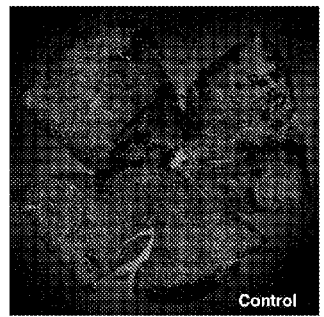
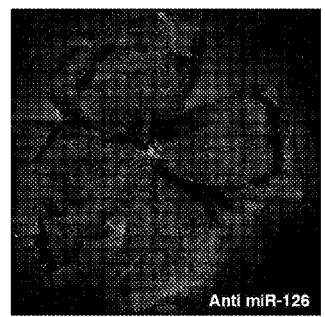
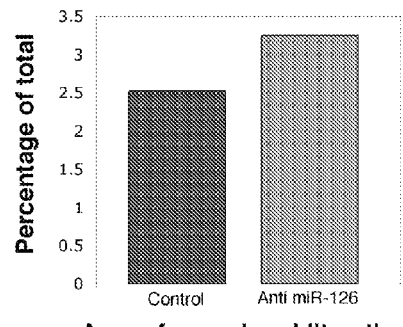
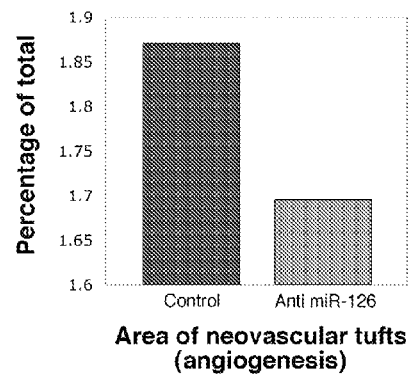
Figure 4B

INHIBITION OF ANGIOGENESIS

This application is a U.S. National Phase Application of International Patent Application No. PCT/US2009/039808 filed Apr. 7, 2009 and entitled "Inhibition of Angiogenesis," which claims the benefit of the filing date of U.S. Provisional Patent Application No. 61/042,936 filed Apr. 7, 2008 and entitled "Inhibitory RNAs that Regulate Vascularization," each of which is incorporated by reference in its entirety.

SEQUENCE LISTING

The instant application contains a Sequence Listing which has been submitted in ASCII format via EFS-Web and is hereby incorporated by reference in its entirety. Said ASCII copy, created on Mar. 18, 2013, is named 2002895.123US2_SL.txt and is 11,590 bytes in size.

For the purpose of the U.S. and other PCT contracting states that permit incorporation by reference only, all patents, patent applications and publications cited herein are hereby incorporated by reference in their entirety.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND

Angiogenesis, the formation of new blood vessels, occurs in the healthy body for healing wounds, for restoring blood flow to tissues after injury, and in certain other situations. In the absence of disease, the angiogenic process is normally tightly controlled by various positive and negative regulatory factors. Excessive angiogenesis is a factor in several pathological conditions. For example, abnormal neovascularization is a factor in various eye diseases, where it may result in hemorrhage and functional disorders of the eye, contributing to the loss of vision associated with retinopathy of prematurity, diabetic retinopathy, retinal vein occlusion, age-related macular degeneration, and other eye diseases (see, for example, Yoshida et al., 1999, Histol Histopathol. 14(4):1287-94). These conditions are leading causes of blindness (Aiello, 1997, Ophthalmic Res. 29(5):354-62). Excessive angiogenesis also plays a role in other disease conditions such as rheumatoid arthritis, and psoriasis. Furthermore, angiogenesis plays an important role in the growth and metastasis of tumors. Indeed several angiogenesis inhibitors are used clinically in the treatment of cancer. Accordingly, there is a need in the art for new and improved angiogenesis inhibitors.

SUMMARY OF THE INVENTION

The present invention is based, in part, on the discovery that the micro-RNA miR-126 plays a functional role in the angiogenic process and that inhibitors of miR-126 block pathologic angiogenesis in vivo.

Accordingly, in one aspect, the present invention provides a method of inhibiting angiogenesis in a subject in need thereof, the method comprising administering to the subject an effective amount of an inhibitor of miR-126. In certain aspects, the subject in whom angiogenesis is to be inhibited has rheumatoid arthritis, psoriasis, or cancer. In other aspects, the subject in whom angiogenesis is to be inhibited has an eye condition or disease associated with excessive blood vessel growth, such as, for example, ocular neo-vascularization, retinopathy of prematurity, diabetic retinopathy, retinal vein occlusion, age-related macular degeneration, posterior uveitis, pathologic myopia, and choroidal arteriosclerosis. The present invention provides methods for the treatment of such diseases and conditions.

The methods of the invention may be used to inhibit angiogenesis, or to treat a condition or disease, in any subject in need thereof, such as in any animal species. In certain embodiments, the subject is a mammal. In preferred embodiments, the subject is a human.

The methods of the invention may also be used to reduce the amount of miR-126 in a cell, or inhibit the expression, function, or activity of miR-126 in a cell, by contacting the cell with an effective amount of an inhibitor of miR-126. The cell may be any cell in which miR-126 is expressed, including a cell in an animal or a cell that is maintained in vitro. In a preferred embodiment, the cell is an endothelial cell.

The miR-126 inhibitors of the invention may be any type of agent that is capable of binding to miR-126. In certain embodiments, the miR-126 inhibitors of the invention are nucleic acid-based molecules. In preferred embodiments, the nucleic acid-based inhibitors of the invention are antisense oligonucleotides. Such antisense oligonucleotides may comprise, for example, ribonucleotides, deoxyribonucleotides, 2'-modified nucleotides, phosphorothioate-linked deoxyribonucleotides, peptide nucleic acids (PNAs), locked nucleic acids (LNAs), or other forms of naturally or non-naturally occurring nucleotides. For example, in one embodiment, the miR-126 inhibitors of the invention are, or comprise, morpholinos or antagomirs.

In preferred embodiments, the miR-126 inhibitors of the invention comprise a nucleotide sequence that forms a duplex with SEQ ID. NO. 1 and/or SEQ ID NO. 2, as provided herein. In other preferred embodiments, the miR-126 inhibitors of the invention comprise the nucleotide sequence of SEQ ID. NO. 4, SEQ ID. NO. 5, or SEQ ID. NO. 6, as provided herein.

The present invention also provides isolated nucleic acids that are capable of forming a duplex with SEQ ID. NO. 1 and/or SEQ ID NO. 2, such as nucleotides having the sequence of SEQ ID. NO. 4, SEQ ID. NO. 5, or SEQ ID. NO. 6, as provided herein.

The present invention also provides pharmaceutical compositions comprising the miR-126 inhibitors of the invention, and expression vectors containing nucleic acids that encode the miR-126 inhibitors of the invention.

These and other embodiments of the invention are described throughout this application, including in the Example section and in the claims.

BRIEF DESCRIPTION OF THE FIGURES

FIG. 2A shows representative images of retinal vasculature in the control situation and following treating with a 2'O-Me modified miR-126 inhibitor (having the sequence of SEQ ID NO: 4). FIG. 2B shows quantitation of vascular obliteration and angiogenic tufts from injections in 6 mice.

FIG. 3. 2'O-Me miR-126 decreases vascularization in the neonatal retina in the oxygen induced retinopathy model.

FIG. 4. miR-126 decreases vascularization in the neonatal retina in the oxygen induced retinopathy model. FIG. 4A shows representative images of retinal vasculature in the control situation and following treating with an oligonucleotide antisense to miR-126 that is phosphorothioate linkage modified, and 2'-OMe-modified. And has cholesterol linked through a hydroxyprolinol linkage: 5'$G_SC_S$AUUAUUACU-CACGGUAC$_S$G$_S$A 3'Chol (SEQ ID NO: 5, Subscript s represents a phosphorothioate linkage) and the control. FIG. 4B shows quantitation of vascular obliteration and angiogenic tufts from injections in 6 mice.

DETAILED DESCRIPTION OF THE INVENTION

Figure 1:
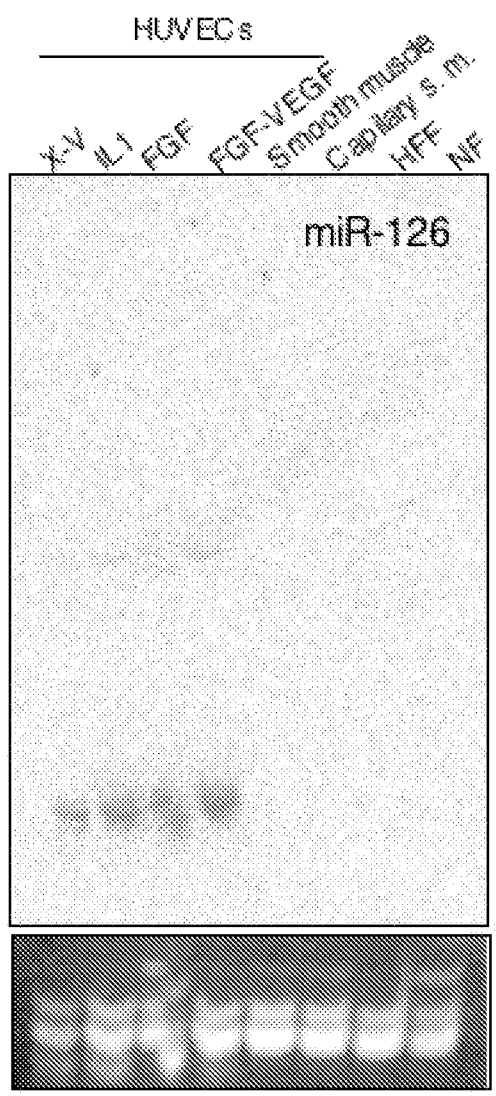
FIG. 1. Northern blot showing miR-126 expression in endothelial cells treated with different cytokines but not in other cell types such as smooth muscle cells and fibroblasts.

The present invention is based on the discovery that the micro-RNA miR-126 plays a functional role in the angiogenic process and that inhibitors of miR-126 block pathologic angiogenesis in vivo. Accordingly, the present invention provides inhibitors of miR-126 that are useful for the inhibition of angiogenesis, and which may be used, for example, in the treatment of conditions that involve abnormal excessive or unwanted blood vessel growth. These and other aspects of the invention are described herein.

DEFINITIONS

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Conditions Involving Angiogenesis

The process of angiogenesis, which may also be referred to herein as neovascularization, is a fundamental process by which new blood vessels are formed. The process involves the migration of vascular endothelial cells into tissue followed by the condensation of such endothelial cells into vessels. Angiogenesis may be induced by an exogenous angiogenic agent or may be the result of a natural condition. The process is essential to a variety of normal body activities such as reproduction, development and wound repair. Although the process is not completely understood, it involves a complex interplay of molecules that stimulate and molecules that inhibit the growth and migration of endothelial cells, the primary cells of the capillary blood vessels. Under normal conditions, these molecules appear to maintain the microvasculature in a quiescent state (i.e., without capillary growth) for prolonged periods which can last for several years or even decades. The turnover time for an endothelial cell can be about one thousand days. However, under appropriate conditions (e.g., during wound repair), these same cells can undergo rapid proliferation and turnover within a much shorter period, and a turnover rate of five days can be typical under these circumstances. (Folkman and Shing, 1989, J. Biol. Chem. 267(16):10931-10934; Folkman and Klagsbrun, 1987, Science 235:442-447).

Although angiogenesis is a highly regulated process under normal conditions, many diseases (characterized as "angiogenic diseases") are driven by, or involve, angiogenesis. In such disease states, angiogenesis can either cause a disease directly or exacerbate an existing pathological condition.

There are many conditions associated with abnormal, excessive or unwanted angiogenesis, and the methods and compositions of the present invention may be useful in the treatment of such conditions.

In the healthy mammalian eye, vessels are excluded from the cornea and from the vitreous, and indeed both compartments can have anti-angiogenic activity (Brem et al., 1977, Am. Ophthalmol. 84:323; Henkind, 1978, Am. Ophthalmol. 85:287; Kaminska and Niederkom, 1993, Invest. Opthalmol. Vis. Sci. 34:222). Failure to exclude vessels from the cornea may be associated with loss of visual acuity, opacification, and abnormal healing (Kaminska and Niederkom, 1993, Invest. Opthalmol. Vis. Sci. 34:222).

Choroidal neovascularization occurs in diseases in which there are abnormalities of Bruch's membrane and/or the retinal pigment epithelium (RPE), the most common of which is age-related macular degeneration (or ARMD). Bruch's membrane is a five-layered extracellular membrane structure that separates the choriocapillaris from the RPE; it seems to provide a physical and biochemical barrier to vascular invasion of the subretinal space. Choroidal neovascularization can reliably be produced in experimental animals including monkeys and mice, by rupturing Bruch's membrane with laser photocoagulation (Miller et al., 1986; To be et al., 1998).

In addition to ARMD, other ophthalmopathological conditions associated with excessive neovascularization include diabetic retinopathy (DR), pathologic myopia, retinal vein occlusion, retinopathy of prematurity (ROP), and neovascular glaucoma. In these diseases new vessels emanate from the retinal circulation which involves the danger of intraocular hemorrhage and tractional retinal detachment with subsequent visual loss. ROP is a major cause of blindness in children, resulting from oxygen supplementation in the premature neonate which suppresses retinal vascular endothelial growth factor (VEGF) production. Accordingly, the retina of newborns showing hyperoxia-induced regression of retinal vessels becomes ischemic when it is exposed to normal room air. This condition, in turn, causes stimulation of retinal neovascularization.

Diabetic retinopathy (DR) is a complication of the chronically high blood sugar afflicting diabetics. It is caused by leakiness of retinal blood vessels and the growth of new blood vessels on the retina, optic nerve and the iris. The leaky blood vessels result in swelling of the retina and visual loss. Pathomechanisms of DR involve capillary occlusion or loss, endothelial cell damage, reduced retinal blood flow with subsequent local ischemia, neovascularization, and breakdown of the blood-retinal barrier. The new blood vessels that grow on the optic nerve and retina can also bleed, resulting in severe visual loss. In addition, new blood vessels in the iris clog the drain of the eye and can result in extremely high pressure in the eye with accompanying intense pain and the potential loss of the eye. DR can affect almost anyone with diabetes. In general, the longer someone has diabetes, the greater the risk of developing DR. Eventually, almost everyone with juvenile-onset diabetes will develop some symptoms of DR. Those who acquire diabetes later in life are also at risk of DR.

The compositions and methods of the invention may be used in the treatment and/or prevention of the conditions described above, including but not limited to, retinopathy of prematurity, diabetic retinopathy, retinal vein occlusion, age-related macular degeneration (or ARMD), posterior uveitis, pathologic myopia, and choroidal arteriosclerosis. Those of skill in the art will be aware of other conditions of the eye that are associated with abnormal angiogenesis. All such conditions are within the scope of the invention, and the compositions and methods of the invention may be used in the treatment or prevention of all such conditions of the eye that are associated with abnormal excessive angiogenesis.

The growth and metastasis of solid tumors is often angiogenesis-dependent (J. Folkman, Cancer Res., 46:467-473 (1986), J. Folkman, J. Natl. Cancer Inst., 82:4-6 (1989)). Tumors which enlarge to greater than 2 mm can obtain their own blood supply by inducing the growth of new capillary blood vessels. Once these new blood vessels become embedded in the tumor, they provide a means for tumor cells to enter the circulation and metastasize to distant sites such as the liver, lungs, and bones (N. Weidner, et. al., N. Engl. J. Med., 324:1-8 (1991)). Indeed, tumor-induced angiogenesis is often required for tumor growth.

Several anti-cancer drugs work by inhibiting tumor angiogenesis. Similarly, the compositions and methods of the invention may be used to inhibit the growth and/or metastasis of tumors in cancers including, but not limited to, breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma, skin cancer (e.g., melanoma), lymphomas and other blood cancers.

In addition, abnormal angiogenesis is associated with conditions including but not limited to rheumatoid arthritis, psoriasis, and various inflammatory disease. For example, in arthritis newly formed capillary blood vessels may invade the joints and destroy cartilage. The compositions and methods of the invention may be used in the treatment or prevention such conditions.

MicroRNA miR-126

MicroRNAs (miRNAs) are a class of single-stranded non-coding RNAs (ncRNAs) that have been conserved in evolution from plants to animals. Mature miRNAs are typically around 17-24 nucleotides in length, but may be longer or shorter. They are generated in cells from miRNA precursors as the result of a series of RNA processing steps. First a pri-miRNA transcript having a hairpin structure is produced. The mature miRNA is located within one arm/strand of this precursor hairpin (the opposite strand of the hairpin, known as the star(*) strand, is generally degraded (see Wang et al., 2008, Dev. Cell, 15, p 261-271)). The pri-miRNA is processed in the nucleus to form a pre-miRNA which is exported to the cytoplasm. The pre-miRNA undergoes further processing in the cytoplasm to form the mature miRNA. It is the mature miRNA that inhibits expression of its target gene at the post-transcriptional level by binding to the mRNA of the target gene by Watson-Crick base pairing. miRNAs have been found to have roles in a variety of biological processes including developmental timing, differentiation, apoptosis, cell proliferation, organ development, and metabolism.

The present invention is related to a microRNA known as miR-126. MiR-126 is derived from one strand of its hairpin precursor, while miR-126* (a distinct sequence) is derived from the opposite strand of the same hairpin precursor (as illustrated in Wang et al., 2008, Dev. Cell, 15, p 261-271, the contents of which are hereby incorporated by reference).

Previous studies showed that miR-126 is enriched in tissues with a vascular component, such as heart and lung (see Lagos-Quintana et al., 2002 Current Biology, 12, p735-739, and Wienholds et al., 2005, Science, 309, p310-311). However, prior to the present invention, little was known about the function of miR-126. As described more fully in the Examples section of this application, the present invention is based, in part, on the discovery that miR-126 regulates angiogenesis in vivo, and the discovery that pathologic angiogenesis can be inhibited in vivo using inhibitors of miR-126.

As used herein, the term "miR-126" is used to refer to a miRNA having the sequence UCGUAC-CGUGAGUAAUAAUGCG (22 nucleotides, SEQ ID NO. 2, see Table 1) or UCGUACCGUGAGUAAUAAUGC (SEQ ID NO. 1, which comprises the first 21 nucleotides of SEQ ID No. 2, see Table 1), and to homologues thereof. The sequence of miR-126 has been highly conserved in evolution and is 100% conserved between humans, rats, dogs, chickens, zebrafish, and Fugu, as illustrated in Wang et al., 2008, Dev. Cell, 15, p 261-271.

In some embodiments, the present invention is directed to miR-126 and to nucleotides having or comprising SEQ ID NO. 1 or SEQ ID NO. 2 and homologues thereof. In addition, the present invention is directed to fragments and variants of SEQ ID NO.s 1 and 2 that bind to the miR-126 target gene(s) and modulate angiogenesis. Accordingly, the present invention fragments and variants of SEQ ID NO.s 1 and 2 having greater than about 70%, or greater than about 75%, or greater than about 80%, or greater than about 85%, or greater than about 90%, or greater than about 95%, or greater than about 99% of their nucleotides identical to those of SEQ ID NOs 1 or 2, and that bind to the miR-126 target gene(s) and modulate angiogenesis. In addition, the present invention also provides fragments and variants of SEQ ID NO.s 1 and 2 that differ from SEQ ID NO.s 1 and 2 by a certain number of nucleotides. For example, in one embodiment, the present invention provides sequences that differ from SEQ ID NOs: 1 or 2 by no more than 10 nucleotides, or no more than 9 nucleotides, or no more than 8 nucleotides, or no more than 7 nucleotides, or no more than 6 nucleotides, or no more than 5 nucleotides, or no more than 4 nucleotides, or no more than 3 nucleotides, or no more than 2 nucleotides, or no more than 1 nucleotide, and that bind to the miR-126 target gene(s) and modulate angiogenesis.

In preferred embodiments, the present invention is related to inhibitors of miR-126 and to methods of inhibiting angiogenesis using such inhibitors, as described more fully below.

TABLE 1

Nucleotide Sequences

| SEQ ID: NO. | SEQUENCE | Comments |
|---|---|---|
| SEQ ID: NO 1 | UCGUACCGUGA GUAAUAAUGC | MiR-126 |
| SEQ ID: NO 2 | UCGUACCGUGA GUAAUAAUGCG | MiR-126 |
| SEQ ID NO: 3 | CGCUGGCGACG GGACAUUAUUA CUUUUGGUACG CGCUGUGACAC UUCAAACUCGU ACCGUGAGUAA UAAUGCGCCGU CCACGGCA | MiR-126 precursor |
| SEQ ID NO: 4 | GCAUUAUUACU CACGGUACGA | miR-126 inhibitor |
| SEQ ID NO: 5 | G$_s$C$_s$AUUAUUAC UCACGGUAC$_s$G$_s$ A-Chol | Phosphorothioate linkage modified 2'-OMe-miR-126 inhibitor, with cholesterol linked through a hydroxyprolinol linkage. Subscript s represents a phosphorothioate linkage. |
| SEQ ID NO: 6 | CGCAUUAUUAC UCACGGUACGA | miR-126 inhibitor |

Inhibitors of miR-126

In one aspect, the present invention provides "inhibitors of miR-126" or "miR-126 inhibitors", and also compositions comprising such inhibitors and methods for inhibiting angiogenesis comprising the use of such inhibitors. Any miR-126 inhibitor may be used in conjunction with the present invention. For example, in one aspect the present invention encompasses small molecule inhibitors of miR-126. In a preferred aspect the miR-126 inhibitors of the invention are "nucleic acid-based" inhibitors of miR-126 that are capable of forming a duplex with miR-126 by Watson-Crick type base pairing.

Any nucleic acid-based inhibitor that is capable of forming a duplex with miR-126, i.e. with SEQ ID NO. 1 or SEQ ID NO. 2 (as illustrated in Table 1), in the cell and inhibiting its function may be used in accordance with the present invention, regardless of the actual mechanism by which the inhibitor works. For example, it is possible that a nucleic acid-based inhibitor of miR-126 may form a duplex with miR-126 sequences and prevent proper processing of the mature miR-126 product from its precursor, or may prevent the mature miR-126 from binding to its target gene, or may lead to degradation of miR-126 or may act through some other mechanism. In a preferred embodiment, the acid-based miR-126 inhibitors of the invention are antisensense oligonucleotides. In a preferred embodiment, the nucleic acid-based miR-126 inhibitors of the invention inhibit the pro-angiogenic effects of miR-126 and/or inhibit angiogenesis in vivo. In vivo inhibition of angiogenesis by candidate miR-126 inhibitors can be assessed using the oxygen-induced retinopathy mouse model described in the Example section of this application, or by any other suitable model for angiogenesis known in the art.

Figure 5:
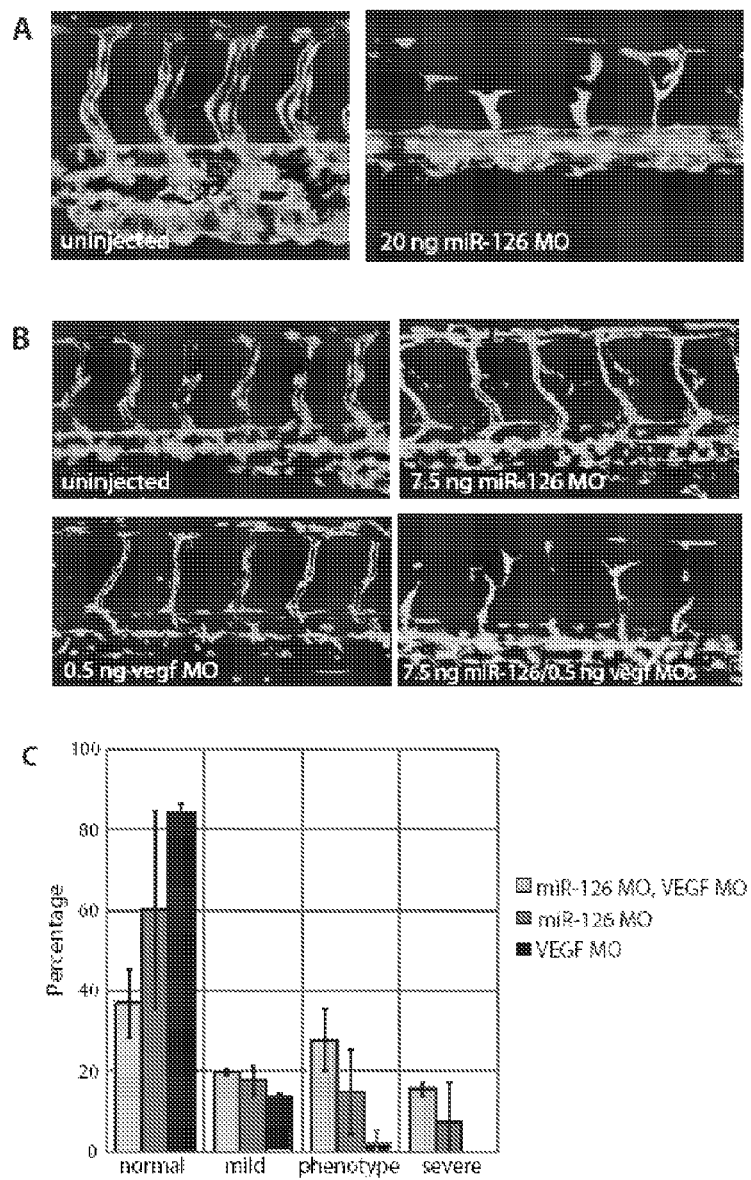
FIG. 5. miR-126 is required for normal patterning in zebrafish and may interact with the VEGF-A pathway. (A) Confocal image of Tg(fli1:EGFP)y1 zebrafish uninjected (left) and injected with 20 ng miR-126 morpholino (right). (B) confocal images of representative morphant fish injected with mir-126 MO. VEGF-A MO or both together. (C) Phenotypic analysis of morphant fli-1 gfp zebrafish. VEGF-A MO (0.5 ng) and miR-126 MO (7.5 ng) alone did not cause a significant angiogenic phenotype, whereas both morpholinos combined caused a severe angiogenic phenotype as evaluated by as masked observer.

As described above, the nucleic acid-based miR-126 inhibitors of the invention are capable of forming a duplex with miR-126, i.e. with SEQ ID NO. 1 or SEQ ID NO. 2, under cellular conditions. In a preferred embodiment, the miR-126 inhibitors of the invention are 100% complementary to SEQ ID NO. 1 or SEQ ID NO. 2, or comprise a string of 12-22 contiguous nucleotides that are 100% complementary to SEQ ID NO. 1 or SEQ ID NO. 2. For example, preferred miR-126 inhibitors that are 100% complementary to miR-126 are illustrated in SEQ ID NO.s 4, 5, and 6, as illustrated in FIG. 5. As described above, the mir-126 inhibitors described herein may comprise deoxyriboynucleotides or ribonucleotides, or modified derivatives or variants of deoxyriboynucleotides or ribonucleotides.

It is well known in the art that while in deoxyribonucleic acids the complementary nucleotide to Adenosine ("A") is thymidine ("T"), in ribonucleic acids the complementary nucleotide to A is uracil ("U"). Thus, the nucleotide T in a deoxyribonucleic acid is the equivalent of the nucleotide U in a ribonucleic acid, and vice versa.

Accordingly, because the miR-126 inhibitors of the present invention may comprise or consist of either deoxyriboynucleotides or ribonucleotides, it is to be understood that every miR-126 inhibitor sequence that is illustrated as comprising the deoxyribonucleotides A, C, T, and G, can equally comprise the ribonucleotides A, C, U, and G, where every position that is a T in the deoxyribonucleotide is substituted with a U in the ribonucleotide version, and vice versa.

In some embodiments, the miR-126 inhibitors of the invention are not 100% complementary to SEQ ID NO. 1 or SEQ ID NO. 2, or do not or comprise a string of 12-22 contiguous nucleotides that are 100% complementary to SEQ ID NO. 1 or SEQ ID NO. 2, but instead contain some mismatched bases. It is not necessary that there be perfect complementarity between the miR-126 inhibitor and miR-126. Thus these miR-126 inhibitors may have one or more regions of non-complementarity with miR-126 flanked by one or more regions of complementarity sufficient to allow duplex formation. It is preferred that the regions of complementarity be at least 8, 9, or 10 nucleotides long. In a preferred embodiment, the nucleic acid based miR-126 inhibitors of the invention are "substantially complementary" to, or comprise one or more regions that are "substantially complementary" to, SEQ ID NO. 1 or SEQ ID NO. 2, or a fragment thereof, meaning that even though not 100% complementary the inhibitors are capable of forming a duplex with SEQ ID NO. 1 or SEQ ID NO. 2 by Watson-Crick type base pairing that is sufficient to result in the inhibition of the function and/or the pro-angiogenic effect of miR-126 in vivo, and/or to inhibit angiogenesis in vivo.

Accordingly, the present invention encompasses miR-126 inhibitors having greater than about 70%, or greater than about 75%, or greater than about 80%, or greater than about 85%, or greater than about 90%, or greater than about 95%, or greater than about 99% of their nucleotides identical to those of SEQ ID NOs 4, 5, or 6, provided herein, or having greater than about 70%, or greater than about 75%, or greater than about 80%, or greater than about 85%, or greater than about 90%, or greater than about 95%, or greater than about 99% of their nucleotides that are complementary to SEQ ID NO.s 1 or 2.

In addition, the present invention also provides miR-126 inhibitors that differ from those of SEQ ID NOs 4, 5, or 6 by only a certain number of nucleotides. For example, in one embodiment, the present invention provides sequences that differ from any of SEQ ID NOs: 4-6 by no more than 10 nucleotides, or no more than 9 nucleotides, or no more than 8 nucleotides, or no more than 7 nucleotides, or no more than 6 nucleotides, or no more than 5 nucleotides, or no more than 4 nucleotides, or no more than 3 nucleotides, or no more than 2 nucleotides, or no more than 1 nucleotide. Similarly, the present invention provides miR-126 inhibitors that are not 100% complementary to SEQ ID NOs. 1 or 2, but that contain mismatches at no more than 10 nucleotide positions, or more preferably no more than 9 positions, or more preferably no more than 8 positions, or more preferably no more than 7 positions or more preferably no more than 6 positions or more preferably no more than 5 positions or more preferably no more than 4 positions or more preferably no more than 3 positions or more preferably no more than 2 positions or more preferably no more than 1 nucleotide position.

One of skill in the art can readily produce such miR-126 inhibitors using standard oligonucleotide synthesis and molecular biology methods, and can readily test such inhibitors to select those that are capable of forming a duplex with miR-126 and/or that are capable of inhibiting the function and/or the pro-angiogenic effect of miR-126 in vivo, and/or inhibiting angiogenesis in vivo. The ability of a candidate miR-126 inhibitors to form a duplex with miR-126 should ideally be tested in vivo or at least inside cells. However, candidates can also be tested for their ability to form a duplex with miR-126 in vitro, ideally using hybridization conditions selected to mimic those of the in-cyto environment. By way of reference, "stringent hybridization conditions" are those that allow hybridization between two homologous nucleic acid sequences, but preclude hybridization of random sequences. Hybridization at high temperature and/or low ionic strength is termed high stringency. In contrast, hybridization at low temperature and/or high ionic strength is termed "low stringency," which permits hybridization of less related sequences. Low stringency hybridization is generally performed at 0.15 M to 0.9 M NaCl at a temperature range of 20° C. to 50° C. High stringency hybridization is generally performed at 0.02 M to 0.15 M NaCl at a temperature range of 50° C. to 70° C. Other factors that can affect stringency are the presence of formamide, tetramethylammonium chloride and/or other solvents in the hybridization mixture.

The nucleic acid-based inhibitors of miR-126 of the present invention are preferably single-stranded, or substantially single-stranded antisense oligonucleotides, or at least have an active form within the cell that is single-stranded, or substantially single-stranded. However, the inhibitors may be double-stranded or partially double stranded or may comprise a hairpin structure. As used herein partially double stranded refers to double stranded structures that contain fewer nucleotides in the complementary strand. In general, such partial double stranded agents will have less than 75% double stranded structure, or more preferably less than 50%, or more preferably less than 25%, 20% or 15% double stranded structure.

The nucleic acid based miR-126 inhibitors of the invention may be of any length so long as they are capable of forming a duplex with miR-126 as described above. For example, the nucleic acid based miR-126 inhibitors of the invention may be around 12, 13, 14, 15, 16, 17, 18, 29, 20, 21, or 22 nucleotides in length. Furthermore, the nucleic acid based miR-126 inhibitors of the invention may be longer than 22 nucleotides in length and they may comprise additional nucleotides at either end or internally in addition to those nucleotides that are complementary to miR-126. In preferred embodiments, the miR-126 inhibitors are at least 19 nucleotides in length.

In preferred embodiments the miR-126 inhibitors (and indeed also the miR-126 sequences of the invention) of the present invention comprise nucleotides that have a desirable profile in terms of stability, nuclease resistance, hybridization thermodynamics, cell permeability, and sequence specificity. The nucleic acid-based inhibitors of miR-126 of the present invention may be made of ribonucleic acids, deoxyribonucleic acids, chemical variants or mimics of nucleic acids, or any combination thereof. Accordingly, the nucleic acid-based miR-126 inhibitors of the present invention may comprise naturally occurring or non-naturally-occurring nucleobases, sugars, and covalent internucleoside (backbone) linkages. The following paragraphs provide further details and examples of nucleotides that may be used in the miR-126 sequences and nucleic acid-based miR-126 inhibitors of the invention.

For example, the nucleic acid-based miR-126 inhibitors of the present invention may comprise ribonucleotides, deoxyribonucleotides, 2'-modified nucleotides, phosphorothioate-linked deoxyribonucleotides, peptide nucleic acids (PNAs), locked nucleic acids (LNAs), ethylene nucleic acids (ENA), certain nucleobase modifications such as 2-amino-A, 2-thio (e.g., 2-thio-U), G-clamp modifications, antagomirs, morpholinos, nucleic acid aptamers, or any other type of modified nucleotide or nucleotide derivative that is capable of Watson-Crick type base pairing with an miRNA. For example, in addition to naturally occurring DNA and/or RNA nucleotide bases, non-naturally occurring modified nucleotide bases that can be used in the miR-126 uinhibitors of the invention include, but are not limited tom 8-oxo-guanine, 6-mercaptoguanine, 4-acetylcytidine, 5-(carboxyhydroxyethyl) uridine, 2'-O-methylcytidine, 5-carboxymethylamino-methyl-2-thioridine, 5-carb 1 pseudouridine, beta-D-galactosylqueosine, 2'-Omethylguanosine, inosine, N.sup.6-isopentenyladenosine, 1-methyladenosine, 1-methylpseudouridine, 1-methylguanosine, 1-methylaminomethyllinosine, 2,2-dimethylguanosine, 2-methyladenosine, 2-methylguanosine, 3-methylcytidine, 5-methylcytidine, N.sup.6-methyladenosine, 7-methylguanosine, 5-methylaminomethyluridine, 5-methoxyaminomethyl-2-thiouridine, beta-D-mannosylqueosine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl) N-methylcarbamoyl) threonine, uridine-5-oxyacetic acid methylester uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl) carbamoyl) threonine, 2'-O-methyl-5-methyluridine, 2'-O-methyluridine, wybutosine, and 3-(3-amino-3-carboxypropyl) uridine.

For a review of some of the chemically modified nucleotides that can be used in the miR-126 inhibitors of the present invention, including 2'-O-methyl oligonucleotides, phosphorothioate-linked deoxyribonucleotides, morpholinos, and LNAs, see Esau (2008), Inhibition of MicroRNA with Antisense Oligonucleotides, Methods, vol. 44, p55-60; Summerton (2007), Morpholino, siRNA, and S-DNA Compared, Current Topics in Medicinal Chemistry, vol. 7, p 651-660; and Krutzfeldt et al., 1005, Silencing of microRNAs in vivo with antagomirs, Nature vol. 438, p685-689, the contents of which are hereby incorporated by reference.

In other embodiments, the miR-126 inhibitors of the present invention may include an aminoglycoside ligand, which may improve hybridization properties and/or sequence specificity. Exemplary aminoglycosides include, but are not limited to, glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

The miR-126 inhibitors of the invention can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. A 3' conjugate, such as naproxen or ibuprofen, may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

The 5'-terminus can also be blocked with an aminoalkyl group, e.g., a 5'-O-alkylamino substituent. Other 5' conjugates can inhibit 5'-3' exonucleolytic cleavage. A 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

The miR-126 inhibitors of the present invention can also be attached to a peptide or a peptidomimetic ligand which may affect pharmacokinetic distribution of the miR-126 inhibitor such as by enhancing cellular recognition, absorption and/or cell permeation. The peptide or peptidomimetic moiety can be about 5-50 amino acids long, e.g., about 5, 10, 15, 20, 25, 30, 35, 40, 45, or 50 amino acids long. A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003). Exemplary cell permeation peptides that may be conjugated to the miR-126 inhibitors of the present invention include Penetratin (RQIKIWFQNRRMKWKK) (SEQ ID NO: 9), Tat fragment (GRKKRRQRRRPPQC) (SEQ ID NO: 10), Signal sequence based peptide (GALFLGWLGAAGST-MGAWSQPKKKRKV) (SEQ ID NO: 11), PVEC (LLIILR-RRIRKQAHAHSK) (SEQ ID NO: 12), Transportan (GWTLNSAGYLLKINLKALAALAKKIL) (SEQ ID NO: 13), Amphiphilic model peptide (KLALKLALKAL-KAALKLA) (SEQ ID NO: 14) Arg$_9$(RRRRRRRRR) (SEQ ID NO: 15), Cecropin P1 (SWLSKTAKKLENSAKKRISE-GIAIAIQGGPR) (SEQ ID NO: 16), alpha.-defensin (ACY-CRIPACIAGERRYGTCIYQGRLWAFCC) (SEQ ID NO: 17), b-defensin (DHYNCVSSGGQCLYSACPIFTKIQGT-CYRGKAKCCK) (SEQ ID NO: 18), Bactenecin (RKCRIV-VIRVCR) (SEQ ID NO: 19), PR-39 (RRRPRPPYLPRPRP-PPFFPPRLPPRIPPGFPPRFPPRFPGKR-NH2) (SEQ ID NO: 20) and Indolicidin ILPWKWPWWPWRR-NH2 (SEQ ID NO: 21).

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 22). An RFGF analogue (e.g., amino acid sequence AALLPVLLAAP (SEQ ID NO: 23)) containing a hydrophobic MTS can also be a targeting moiety. The peptide moiety can be a "delivery" peptide, which can carry large polar molecules including peptides, oligonucleotides, and proteins across cell membranes. For example, sequences from the HIV Tat protein (GRKKRRQRRRPPQ (SEQ ID NO: 24)) and the *Drosophila Antennapedia* protein (RQIKIWFQNRRMKWKK (SEQ ID NO: 9)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). The peptide or peptidomimetic which may be tethered to the miR-126 inhibitors of the invention may be a cell targeting peptide such as an arginine-glycine-aspartic acid (RGD)-peptide, or RGD mimic.

In other embodiments, the miR-126 inhibitors of the invention may be attached a cholesterol moiety, e.g., at the 3' or 5' end.

Methods for Characterizing and Identifying miR-126 Inhibitors

The present invention contemplates methods for characterizing and testing known or potential/candidate miR-126 inhibitors as well as methods of screening to identify new miR-126 inhibitors, including small molecule inhibitors, nucleic acid-based inhibitors, and indeed any other agents, e.g., compounds, peptides, polypeptides, or antibodies, in order to identify miR-126 inhibitors. As also described elsewhere in this application, the screening assays of the present invention may be used to test for a variety of properties and/or activities of an miR-126 inhibitor, including, but not limited to, binding to miR-126, decrease in expression of miR-126, degradation of miR-126, inhibition of activity of miR-126, inhibition of binding of miR-126 to its target gene(s), alteration of expression of a miR-126 target gene, effects on cellular function, effects on endothelial cell growth, proliferation or survival, effects on angiogenesis either in ex vivo models or in vivo, effects on a disease or condition of interest, such as tumor angiogenesis of angiogenesis in an eye disease, and the like. There are many suitable screening methods known in the art which may be used in accordance with the present invention. For example, one of skill in the art can readily test for the ability of a candidate mir-126 inhibitor to form a duplex with mir-126 using any of the methods known in the art for testing duplex formation, such as various hybridization based assays, reporter gene assays and the like. For example, the Examples section of this application describes reporter gene assays that can be used to measure binding of mir-126 to its target gene(s).

Various cells naturally express miR-126 and can be utilized for testing miR-126 inhibitors and candidate miR-126 inhibitors. Of particular interest are endothelial cells, and progenitors therefor. Other cells may be engineered to express miR-126, for example from a construct containing a screenable marker, permitting one to assess the effects of a candidate substance on the expression, function, or activity of miR-126 in those cells in vitro or in vivo.

For example, in one embodiment, the present invention may be used to screen miR-126 inhibitors for their ability to treat ocular disease, or cause, prevent or delay the onset of ocular disease. Accordingly, in one aspect, the present invention provides for a method for determining whether a candidate miR-126 inhibitor is capable of inhibiting miR-126 in vivo in the eye, the method comprising (a) administering a candidate miR-126 inhibitor to one test eye of a subject with an ocular disease; (b) measuring expression or activity of miR-126 in the test eye of the subject, and (c) comparing the expression or activity of miR-126 measured in the test eye to that of the control eye which was not injected with the candidate miR-126 inhibitor or which was injected with a control substance (such as the injection vehicle alone or another non-specific compound or oligonucleotide), wherein a decrease in the expression of miR-126 in the test eye as compared to the control eye indicates that the test compound may be a useful miR-126 inhibitor. Multiple variations of the above screening method can be used. For example, one can compare the level of angiogenesis in the control versus test eye, or compare the level of disease in the control versus test eye, or compare visual acuity or some read out of visual function in the control versus test eye. The screening methods provided in the Examples section of this application provide one preferred method that can be used to screen for miR-126 inhibitors. Furthermore, candidate miR-126 inhibitors can be screened for a variety of different activities including for their effects on angiogenesis in various model systems such in vitro tissue culture angiogenesis models, matrigel plug angiogenesis models, chick chorionic allantois angiogenesis models, in vivo tumor angiogenesis models, various other animal models, and the like. For example, areas of neovascularization in a test subject, such as a mouse, can be measured before and after administration of a known or candidate miR-126 inhibitor. A reduction in the area or amount of neovascularization following administration of such a known or candidate miR-126 inhibitor is indicative of a potentially useful miR-126 inhibitor. Techniques for observing and measuring the size of neovascularized areas in a subject are within the skill in the art; for example, areas of choroid neovascularization can be observed by ophthalmoscopy. Inhibition of angiogenesis can also be inferred through observing a change or reversal in a pathogenic condition associated with the angiogenesis. For example, in ARMD, a slowing, halting or reversal of vision loss may indicate an inhibition of angiogenesis in the choroid. For tumors, a slowing, halting- or reversal of tumor growth, or a slowing or halting of tumor metastasis, may indicate an inhibition of angiogenesis at or near the tumor site. These and other variations in the screening methods described herein will be apparent to those of skill in the art.

As regards candidate compounds for testing, one may simply acquire, from various commercial sources, libraries of molecules (such as small molecules or antisense oligonucleotides) to use in a "brute force" effort for the identification of miR-126 inhibitors. Indeed microRNA inhibitors and libraries of microRNA inhibitors are available from commercial sources such as Ambion Inc., dPharmaco, and Exiqon, to name but a few. Screening of such inhibitors and inhibitor libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate miR-126 inhibitors may include fragments or parts of naturally-occurring compounds or may be found as active combinations of known compounds which are otherwise inactive. Compounds isolated from natural sources, such as animals, bacteria, fungi, plant sources, including leaves and bark, and marine samples may be assayed as candidates for the presence of potentially useful pharmaceutical agents. The pharmaceutical agents to be screened can also be derived or synthesized from chemical compositions or man-made compounds. Thus, the candidate substance identified by the present invention may, for example, a polypeptide, polynucleotide, small molecule inhibitor, or any compound or agent that may be developed through rational drug design starting from known compound/agent.

Production of miR-126 Inhibitors

The nucleic acid based miR-126 inhibitors of the invention can be synthesized in vitro by chemical synthesis using standard oligonucleotide synthesis methodology known to those of skill in the art. For example, the miR-126 inhibitors of the present invention can be made using standard technology used to make synthetic oligonucleotides, such as methods that use phosphotriester, phosphite or phosphoramidite chemistry and solid phase techniques, such as those described in EP 266 032, the contents of which are hereby incorporated by reference, or via deoxynucleoside H-phosphonate intermediates as described by Froehler et al. (1986) and U.S. Pat. No. 5,705,629, each of which is incorporated herein by reference. Various different mechanisms of nucleic acid synthesis have been disclosed in for example, U.S. Pat. Nos. 4,659,774, 4,704,362, 4,816,571, 5,141,813, 5,264,566, 4,959,463, 5,221,619, 5,428,148, 5,554,744, 5,574,146, 5,602,244, and 5,583,013, each of which is incorporated herein by reference. Furthermore, one can order the miR-126 inhibitors of the invention from one of the many commercial enterprises that produces custom oligonucleotides, including modified oligonucleotides suitable for delivery to cells for microRNA inhibition.

Alternatively, the miR-126 inhibitors of the invention can be expressed in a cell, for example by expression from an expression vector which comprises the nucleotide sequence encoding the miR-126 inhibitor operably linked to a suitable promoter. The cell can be any desired cell. In a preferred embodiment, the cell is am endothelial cell, a smooth muscle cell, a vascular cell, a HUVEC cell, a HMVEC cell, or a pluripotent stem cell. Methods of expressing nucleotide sequences in cells from expression vectors are well known in the art, and can be readily performed without undue experimentation (see for example Couture et al., Trends in Genetics 12:510, 1996). For example, the expression vectors can be DNA plasmids or viral vectors. Oligonucleotide agent-expressing viral vectors can be constructed based on, but not limited to, adeno-associated virus, retrovirus, adenovirus, or alphavirus. In another embodiment, pol III based constructs may be used to express nucleic acid molecules of the invention (see for example Thompson, U.S. Pat. Nos. 5,902,880 and 6,146,886). Vectors for expression of miR-126 inhibitors may be delivered to cells using any suitable transfection method, such as those described herein, and may persist in, or stably integrate into the genome of, target cells. Alternatively, expression vectors may be used that provide for transient expression of the miR-126 inhibitors of the invention. Such expression vectors can be repeatedly administered as necessary.

In certain embodiments, the invention provides a transgenic non-human mammal whose somatic and/or germ cells comprise a nucleic acid of the present invention, wherein the nucleic acid is operably linked to a promoter. In one embodiment, the promoter is a constitutively active promoter or an inducible promoter. In another embodiment, the promoter is a cell specific promoter. In still a further embodiment, the promoter is a cell specific promoter, wherein the cell for which the promoter is specific is an endothelial cell, a smooth muscle cell, a vascular cell, a HUVEC cell, a HMVEC cell, or a pluripotent stem cell.

In certain embodiments of the invention, cells containing a nucleic acid construct of the present invention may be identified in vitro or in vivo by including a marker in the expression vector. Such markers can confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Usually the inclusion of a drug selection marker aids in the cloning and identification of transformants/transfectants, for example, genes that confer resistance to agents including, but not limited to, neomycin, puromycin, hygromycin, DHFR, GPT, zeocin and histidinol are useful selectable markers. In addition to markers conferring a phenotype that allows for the discrimination of transformants/transfectants based on the implementation of conditions, and other types of markers, including screenable markers such as GFP or luciferase can also be used. Alternatively, screenable enzymes such as herpes simplex virus thymidine kinase (tk) or chloramphenicol acetyltransferase (CAT) may be utilized. One of skill in the art will also know how to employ immunologic markers, for example, in conjunction with FACS analysis. The marker used is not believed to be important, so long as it is capable of being expressed simultaneously with the miR-126 inhibitors of the invention. Further examples of selectable and screenable markers are well known to one of skill in the art.

Subjects & Methods of Treatment

The compositions and methods of the present invention can be used to inhibit angiogenesis in any subject in need thereof, including in any animal species in which miR-126 is expressed and in which miR-126 plays a role in the process of angiogenesis. The sequence of miR-126 has been highly conserved throughout evolution and is 100% conserved between humans, rats, dogs, chickens, zebrafish, and Fugu, as illustrated in Wang et al., 2008, Dev. Cell, 15, p 261-271. Accordingly, the compositions and methods of the present invention may be used to inhibit angiogenesis animals including, but not limited to mammals, birds, and fish.

In a preferred embodiment, the compositions and methods of the invention are used to inhibit angiogenesis in mammals. In a more preferred embodiment, the compositions and methods of the invention are used to inhibit angiogenesis humans. The compositions and methods of the invention may be used in the treatment of any condition associated with abnormal, excessive, or unwanted angiogenesis, including, but not limited to, those conditions described herein. For example, in one embodiment, the compositions and methods of the invention are used to inhibit (or arrest, delay or reverse) angiogenesis in a subject having an ocular condition including, but not limited to, ocular neo-vascularization, pathological ocular angiogenesis, choroidal arteriosclerosis, age-related macular degeneration, diabetic retinopathy, retinopathy of prematurity, posterior uveitis, pathologic myopia or any combination thereof.

In addition to treating pre-existing conditions, the miR-126 inhibitors of the present invention can also be administered prophylactically in order to prevent or slow the onset of a disease or disorder. In prophylactic applications, the miR-126 inhibitors of the present invention may be administered to a subject who is susceptible to, or otherwise at risk of, a disorder or condition associated with abnormal, excessive, or unwanted angiogenesis.

Pharmaceutical Compositions

The miR-126 inhibitors of the present invention may be incorporated into any pharmaceutical composition suitable for administration to the subject of choice and suitable for the chosen route of delivery. For example, the miR-126 inhibitors of the present invention can be formulated into a pharmaceutical composition comprising one or more pharmaceutically acceptable carriers. As used herein the term "pharmaceutically acceptable carrier" includes, but is not limited to, solvents, dispersion media, coatings, antibacterial and antifungal agents, isotonic and absorption delaying agents, and the like, compatible with pharmaceutical administration. The use of such pharmaceutical carriers is well known in the art (see, for example, Remington's Pharmaceutical Sciences, 17th Edition, 1985, Publisher: Mack Pub. Co., the contents of which are hereby incorporated by reference).

The exact formulation chosen for the pharmaceutical compositions of the invention will vary depending on the intended delivery route and the desired release profile. For example, formulations suitable for direct injection and parenteral administration may include sterile aqueous solutions which may also contain buffers, diluents, preservative, and other suitable additives, and for intravenous use, the total concentration of solutes may be controlled to render the preparation isotonic. Formulations suitable for sustained release may also be produced, for example where preventative or long-term treatments are desired. One of skill in the art can readily formulate the miR-126 inhibitors of the invention into a pharmaceutical composition suitable for the chosen delivery route and chosen release profile without undue experimentation.

Administration and Delivery

The miR-126 inhibitors of the present invention, whether to be administered as isolated oligonucleotides or to be delivered using an expression vector, can be delivered to a subject by a variety of routes, including, but not limited to oral delivery, parenteral administration, intravenous delivery, intramuscular, subcutaneous delivery, intraperitoneal, intrathecal or intraventricular, delivery by inhalation, oral intrathecal, parenchymal, intravenous, nasal, oral, intratumor delivery, intraocular delivery, topical delivery, (including ophthalmic, intranasal, and transdermal delivery).

The miR-126 inhibitors of the invention can also be administered in a single dose or in multiple doses, as desired, and can be administered in combination with other pharmaceutical agents or treatment regimens if desired, for example, in conjunction with other therapeutic agents designed to inhibit angiogenesis. For example, the miR-126 inhibitors of the present invention can be administered in conjunction with another agent or treatment regimen useful for inhibiting angiogenesis and/or for treating an ocular disease or cancer (such as radiation therapy, chemotherapy, and/or surgery).

In preferred embodiments, the miR-126 inhibitors of the present invention are delivered directly to the cells or tissue in which they are needed, for example the tissue in which it is desired to inhibit angiogenesis. For example, the miR-126 inhibitors of the invention can be delivered directly to the endothelial cells to be targeted, or can be conjugated to a molecule that targets the miR-126 inhibitor to those endothelial cells. In the case of the use of the miR-126 inhibitors of the invention to inhibit tumor angiogenesis, the inhibitors may be delivered directly to the tumor site, for example by direct injection of infusion into the tumor or by conjugating the inhibitors to a molecule that targets the miR-126 inhibitors to the tumor.

In the case of the use of miR-126 inhibitors of the invention to treat conditions of the eye, there are several ways by which the miR-126 inhibitors can be delivered directly to desired area, including, but not limited to, by intraocular injection, by direct injection into a given compartment of the eye, such as the vitreous, the cornea, or the retina, by application of a patch on the eye, by direct application of an ointment, spray, or droppable liquid to the eye. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. Furthermore, the miR-126 inhibitors of the invention can be delivered using an intraocular implant. Such implants can be biodegradable and/or biocompatible implants, or may be non-biodegradable implants. The implants may be inserted into a chamber of the eye, such as the anterior or posterior chambers, or may be implanted in the sclera, transchoroidal space, or an avascularized region exterior to the vitreous. In one embodiment, the implant may be positioned over an avascular region, such as on the sclera, so as to allow for transscleral diffusion of the drug to the desired site of treatment, e.g., the intraocular space and macula of the eye.

In one embodiment, the miR-126 inhibitors of the invention may be administered to cells ex-planted from a subject followed by reintroduction of the cells into the subject, i.e. by ex vivo delivery. Such methods may be particularly desirable in the case of delivery of an expression vector but can also be used for delivery of oligonucleotides. Such ex vivo methods are known in the art. For example, canine endothelial cells have been genetically altered by retroviral gene transfer in vitro and transplanted into a canine (Wilson et al., 1989) and yucatan minipig endothelial cells have been transfected by retrovirus in vitro and transplanted into an artery using a double-balloon catheter (Nabel et al., 1989). Suitable methods that could be used include virtually any method by which a nucleic acid may be delivered to a cell, including, but not limited to, transfection (Wilson et al., 1989, Nabel et al, 1989), by injection (see, for example, U.S. Pat. Nos. 5,994,624, 5,981,274, 5,945,100, 5,780,448, 5,736,524, 5,702,932, 5,656,610, 5,589,466 and 5,580,859), including microinjection (see, for example, Harland and Weintraub, 1985; U.S. Pat. No. 5,789,215); by electroporation (see, for example, U.S. Pat. No. 5,384,253; Tur-Kaspa et al., 1986; Potter et al., 1984); by calcium phosphate precipitation (see, for example, Graham and Van Der Eb, 1973; Chen and Okayama, 1987; Rippe et al., 1990); by using DEAE-Dextran followed by polyethylene glycol (see, for example, Gopal, 1985); by direct sonic loading (see, for example, Fechheimer et al, 1987); by liposome-mediated transfection (see, for example, Nicolau and Sene, 1982; Fraley et al., 1979; Nicolau et al., 1987; Wong et al., 1980; Kaneda et al., 1989; Kato et al., 1991) and receptor-mediated transfection (see, for example, Wu and Wu, 1987; Wu and Wu, 1988); by microprojectile bombardment (see, for example, PCT Application Nos. WO 94/09699 and 95/06128; U.S. Pat. Nos. 5,610,042; 5,322,783 5,563,055, 5,550,318, 5,538,877 and 5,538,880); by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985), and/or any combination of such methods. Some of the above methods may also be used to deliver the miR-126 inhibitors of the invention directly to the subject, i.e. without first removing the cells and supplying the miR-126 inhibitors to the cells ex vivo.

Doses & Effective Amounts

The miR-126 inhibitors of the invention should be administered to a subject in an amount that is effective for the desired purpose, for example in an amount that is effective to inhibit the function of activity of miR-126 or in an amount that is effective to inhibit angiogenesis. One of skill in the art can readily determine a suitable dose for administration by taking into account factors such as the size and weight of the subject; the extent of the neovascularization or disease penetration; the age, health and sex of the subject; the route of administration; and whether the administration is regional or systemic, and by using performing tests using in vitro models or in vivo models using test animals and the like.

EXAMPLES

The examples described below are provided to illustrate aspects of the present invention and are not included for the purpose of limiting the invention. The numbers in parentheses in the below examples refer to the numbered references listed at the end of that example.

Example 1

MicroRNAs (miRNAs) are an abundant class of non-coding RNAs of about 22 nucleotides in length that negatively regulate mRNA translation by binding to partially complementary sequences in their 3' UTRs. They regulate basic cellular functions including proliferation, differentiation, and death. It is now apparent that abnormal miRNA expression is a common feature of human diseases such as cancer, diabetes and heart disease. The results described in this Example show that inhibition of miR-126 by antisense oligonucleotides in the neonatal eye inhibits retinal vascularization. These results can have therapeutic uses for a common cause of blindness, as well as potentially for other diseases and conditions associated with increased or excessive vascularization.

miRNAs were cloned and sequenced from human umbilical vein cells (HUVECs) and human microvascular endothelial cells (HMVECs), to determine the miRNA expression profile from human endothelium (Table 2) miR-126 was among the most abundant miRNAs in the library (6% in HUVECs and 12% in HMVECs), and was much more highly expressed than miR-126*. We confirmed by Northern blotting that miR-126 is highly expressed in endothelium but not in neighboring cell types such as smooth muscle cells (FIG. 1). In addition, miR-126 is reported to be specifically expressed in vascular tissue by in situ hybridization (1, 2). The expression levels of miR-126 in endothelial cells and its specificity to vascular tissues led us to the characterization of miR-126 function in angiogenesis.

TABLE 2 miRNAs cloned from endothelial cells.

| microRNA | Number of sequences cloned | |
|---|---|---|
| | HUVEC | HMVEC |
| let-7b | 2 | 5 |
| miR-18a* | 2 | |
| miR-19a | 1 | |
| miR-21 | 1 | |
| miR-22 | 41 | 44 |
| miR-24 | | 1 |
| miR-27a | 4 | |
| miR-27b | 1 | 3 |
| miR-30e-3p | 1 | |
| miR-31 | 1 | |
| miR-125a | 2 | 1 |
| miR-125b | 2 | 1 |
| miR-126 | 6 | 11 |
| miR-126* | 1 | 1 |

TABLE 2-continued miRNAs cloned from endothelial cells.

| microRNA | Number of sequences cloned | |
|---|---|---|
| | HUVEC | HMVEC |
| miR-127 | 5 | 2 |
| miR-130b | 1 | |
| miR-134 | 1 | |
| miR-140 | | 1 |
| miR-146 | 3 | 3 |
| miR-151 | 1 | 1 |
| miR-181a | 9 | 4 |
| miR-185 | 1 | |
| miR-193 | 1 | |
| miR-221 | 3 | |
| miR-320 | 3 | |
| miR-328 | 2 | 1 |
| miR-339 | 3 | 3 |
| miR-365 | 3 | |
| miR-370 | | 1 |
| miR-491 | | 1 |
| miR-506 | | 1 |
| miR-510 | | 1 |
| miR-513 | | 1 |
| miR-517 | | 1 |
| miR-605 | | 1 |
| miR-609 | | 1 |
| miR-RG-51 | 1 | 3 |
| miR-E1 | 1 | 1 |
| Total | 103 | 94 |

Ocular neovascularization is a common cause of blindness among many age groups: e.g. retinopathy of prematurity in children, diabetic retinopathy in working-age adults and age-related macular degeneration in the elderly. In principle, destructive angiogenesis in the eye can be ameliorated by either direct inhibition of neovascularization or by controlling vessel loss in order to reduce the hypoxic stimulus that drives neovascularization. Retinopathy is modeled in the mouse eye with oxygen-induced vessel loss, which precipitates hypoxia-induced retinopathy, allowing for assessment of retinal vessel loss, vessel regrowth after injury and pathological angiogenesis (3). This mouse model was used to determine whether miR-126 has a role in ocular neovascularization.

Figure 2:
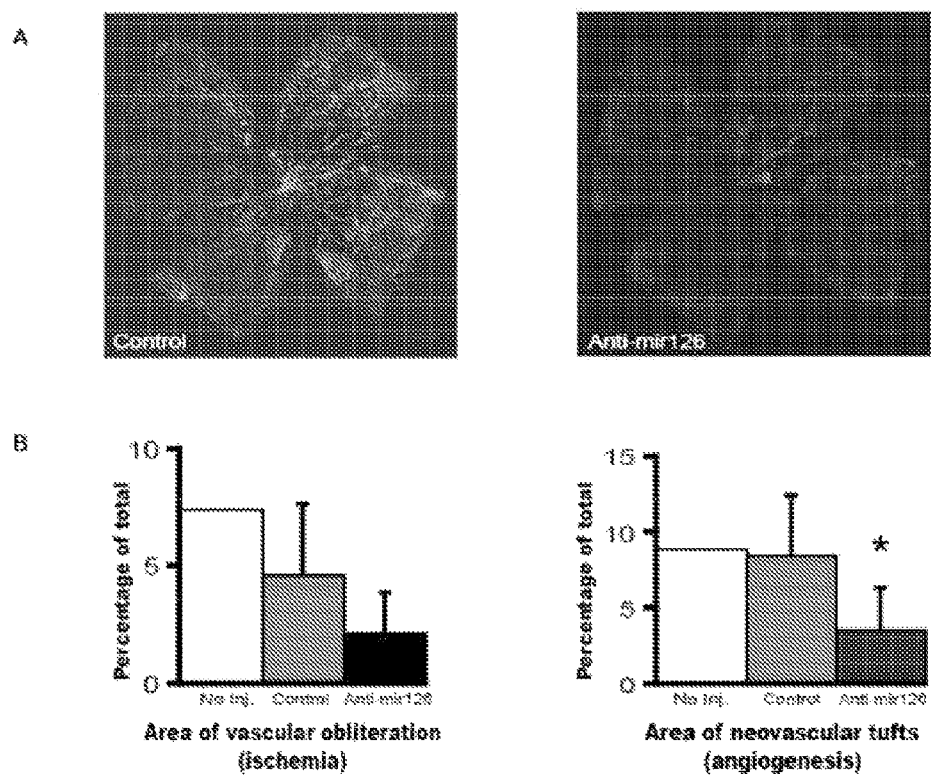
FIG. 2. 2'O-Me miR-126 decreases vascularization in the neonatal retina.
Figures 3A, 3B:
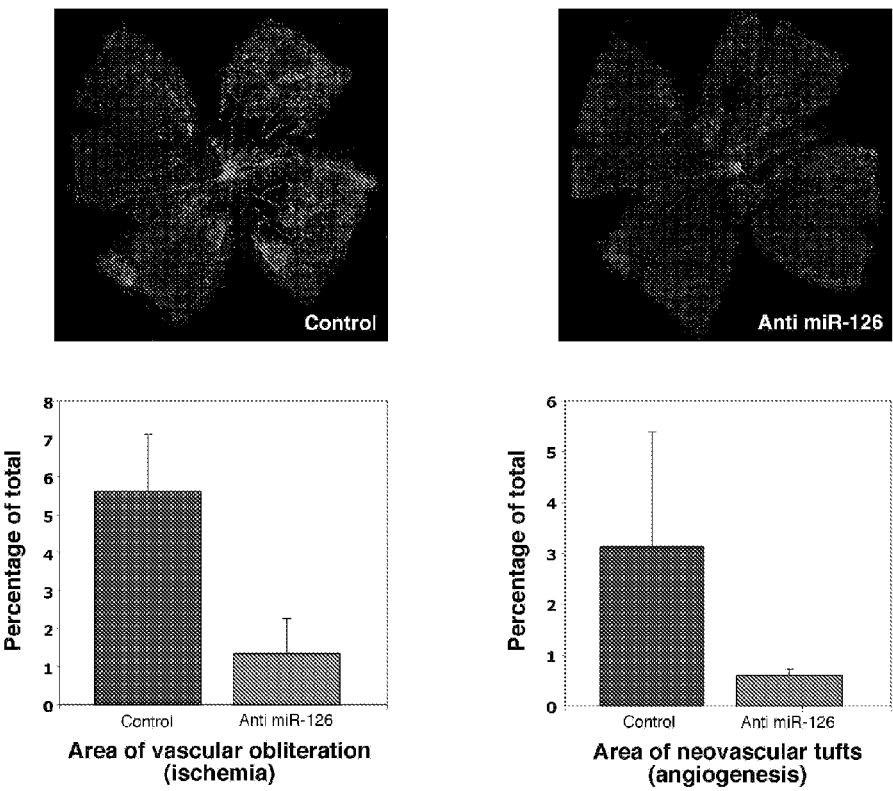
FIG. 3A shows representative images of retinal vasculature in the control situation and following treating with an a 2'O-Me modified miR-126 inhibitor (having the sequence of SEQ ID NO: 4) and the control.
FIG. 3B shows quantitation of vascular obliteration and angiogenic tufts from injections in 6 mice.

Briefly, postnatal day 7 pups C57/BL6/129S were exposed to 75% oxygen for 5 days. At postnatal day 12 the mice received intravitreal injections of 200 pmol 2'O-Methyl oligonucleotide antisense to miR-126 (2'O-Me miR-126), in one eye, and control 2'O-Me oligonucleotide (control) in the other eye. All oligonucleotides were purchased from Dharmacon. Mice were euthanized on post-natal day 17 and retinas were whole mounted and stained with GS-IB4 lectin. Images were captured using a Zeiss LSM 510 confocal microscope and masked to an independent, experienced observer who identified areas of hyaloid (primitive vasculature), vascular obliteration, and pre-retinal neovascular tufts Inhibition of miR-126 resulted in significant decrease of vascular tufts and also in a reduction of the vascular obliterated area (FIGS. 2-4).

Inhibition of miR-126 by antisense oligonucleotides can therefore be of therapeutic significance miR-126 inhibitory oligonucleotides can be used as a sole therapy or in combination with currently used angiogenesis inhibitors, such as, for example, anti-VEGF antibodies.

REFERENCES FOR EXAMPLE 1

1. Kloosterman W P, et al. In situ detection of miRNAs in animal embryos using LNA-modified oligonucleotide probes. Nat. Methods. 2006 January; 3(1):27-9.
2. Wienholds E, et al. MicroRNA expression in zebrafish embryonic development. Science. 2005 Jul. 8; 309(5732): 310-1. Epub 2005 May 26.
3. Smith, L. E. et al. Oxygen-induced retinopathy in the mouse. Invest. Ophthalmol. Vis. Sci. 35, 101-111 (1994).

Example 2

Here we show that the endothelial cell-specific miR-126 supports proper assembly of developing vessels in zebrafish, suggesting that miR-126 regulates the patterning of nascent neo-vessels into stabilized vasculature. In support of this notion, we demonstrate that inhibition of miR-126 abrogates pathologic neovascularization in an oxygen-induced retinopathy (OIR) mouse model of retinopathy of prematurity (ROP), by normalizing the formation of mature vessels from abnormal vasculature. Our results suggest that inhibition of miR-126 by antisense oligonucleotides can be a useful therapeutic intervention for pathologic ocular angiogenesis.

VEGF-A and its receptors play a central role in angiogenesis, and recently VEGF-A neutralizing antibodies have been proven to be effective in rehabilitating vision in age-related macular degeneration (ARMD). However, accumulating evidence suggests that there is a subset of patients that respond poorly to these treatments. Thus, complementary treatments that are not focused on direct inhibition of the VEGF-A pathway are necessary. MicroRNAs have emerged as novel negative regulators of gene expression. They have become an attractive potential therapeutic target because they can be easily inhibited by means of antagonizing antisense oligonucleotides. There have been several studies aiming to identify miRNAs involved in angiogenic pathways, including miR-126 (1-6). We show that the endothelium-specific miR-126 regulates in vivo angiogenesis in development and disease. We show that specific inhibition of miR-126 in zebrafish results in angiogenic defects during embryonic development. Pathologic angiogenesis was inhibited in a mouse model of oxygen-induced retinopathy. These results show that miR-126 plays an important role in blood vessel formation during development by stabilizing nascent vessels, and in sprouting of blood vessels in disease conditions, such as for example in response to ischemic induced retinopathy of prematurity.

Materials and Methods

Oxygen Induced Retinopathy Model

Postnatal day 7 pups C57/BL6/129S were exposed to 75% oxygen for 5 days. At postnatal day 12 they, the mice received intravitreal injections of 200 pmol 2'O-Methyl oligonucleotide antisense to miR-126 (2'O-Me miR-126), in one eye, and control 2'O-Me oligonucleotide (control) in the contralateral eye. Mice were euthanized on post-natal day 17 and retinas were whole mounted and stained with GS-IB4 lectin. Images were captured using a Zeiss LSM 510 confocal microscope and masked to an independent observer who identified areas of hyaloid vasculature, vascular obliteration, and pre-retinal neovascular tufts similar to a technique described previously (7).

Zebrafish Strains and Morpholino Microinjections

Morpholinos were obtained from Gene Tools LLC and dissolved to a concentration 8.69 ng/nl in water. Morpholinos were injected into one- or two-cell-stage embryos at doses between 0.5 ng and 20 ng per embryo, one 2.3 nl of MO solution was injected. miR-126 MO: 5' CGCATTATTACT-CACGGTACGA (SEQ ID NO. 7 is antisense to the mature miR-126 miRNA. Note that SEQ ID NO. 7 is the same as SEQ ID NO. 6 with the exception that SEQ ID No. 7 has T (thymidine) residues at positions in which SEQ ID No. 6 has U (uridine) residues. VEGF morpholino VEGF-A MO 5'-GTATCAAATAAACAACCAAGTTCAT (SEQ ID NO. 8) is a translational blocker (8). Each embryo was injected with: 20 or 7.5 ng miR-126 and/or 0.5 ng VEGF MO in a 2.3 nl volume. Batches of sibling groups were injected and the phenotypes were analyzed after 24 and 48 hours post fertilization (hpf).

HEK293 Cells Expressing Inducible miR-126 pFRT/TO/miR-126 was generated by PCR amplification of the miR-126 locus by restriction digest and ligation into pFRT/TO. HEK293 cells stably expressing miR-126 were generated as described by the manufacturer (Invitrogen). Briefly, Flp-In T-Rex-293 cells (Invitrogen) were grown in Dulbecco's modified Eagle's medium supplemented with 10% FBS, 100 units/ml penicillin, 100 µg/ml streptomycin, 5 µg/ml blasticidin and 100 µg/ml zeocin. Cells were cotransfected with pFRT/TO/miR-126 and pOG44 (Invitrogen). Integration was selected by exchanging the zeocin with 100 µg/ml hygronycin. miR-126 expression was confirmed by Northern hybridization.

Dual Luciferase Assay

Reporter plasmids were made by cloning the 3'UTR of predicted miR-126 targets (www.targetscan.org) into the psicheck2 vector (Promega). The primers are listed in Table 3. HEK293 cells described above were tranfected in 96-well format (40,000 cells/well) with 100 ng reporter psiCHECK vectors with Lipofectamine 2000 (Invitrogen). Cells were lysed 15 h after transfection and analyzed using the Dual-Glo Luciferase Assay System (Promega) as described by the manufacturer on a Spectra Max M2 plate reader).

TABLE 3

Primer Sequences

| Gene | Forward primer 5'-3' | Reverse primer 5'-3' |
| --- | --- | --- |
| FBX033 | ccctagcaaca agtcactgga (SEQ ID NO: 25) | tttaacactaaaag tagtcatgcttca (SEQ ID NO: 32) |
| CDNK2AIP | tgtgtccaaaata tcactgcatacaa (SEQ ID NO: 26) | gaaaattgaagg gaatcgctttt (SEQ ID NO: 33) |
| AKAP13 | acagaaccgctt accaagaactg (SEQ ID NO: 27) | ctggatcaagtt ctggcctctaa (SEQ ID NO: 34) |
| IRS1 | tggtacgatg catccatttc (SEQ ID NO: 28) | atggtgggaa tagagcagga (SEQ ID NO: 35) |
| PFH15 | ggtcacttcca ccactggtaa (SEQ ID NO: 29) | caagtgctga gactgctgga (SEQ ID NO: 36) |
| PLK2 | atggaccta tgggactcct (SEQ ID NO: 30) | ttttcatactct ttattgccaacg (SEQ ID NO: 37) |
| SPRED1 | aatggtccag tgccaaaatg (SEQ ID NO: 31) | acggcaaaat cttagcagca (SEQ ID NO: 38) |

Figure 6:
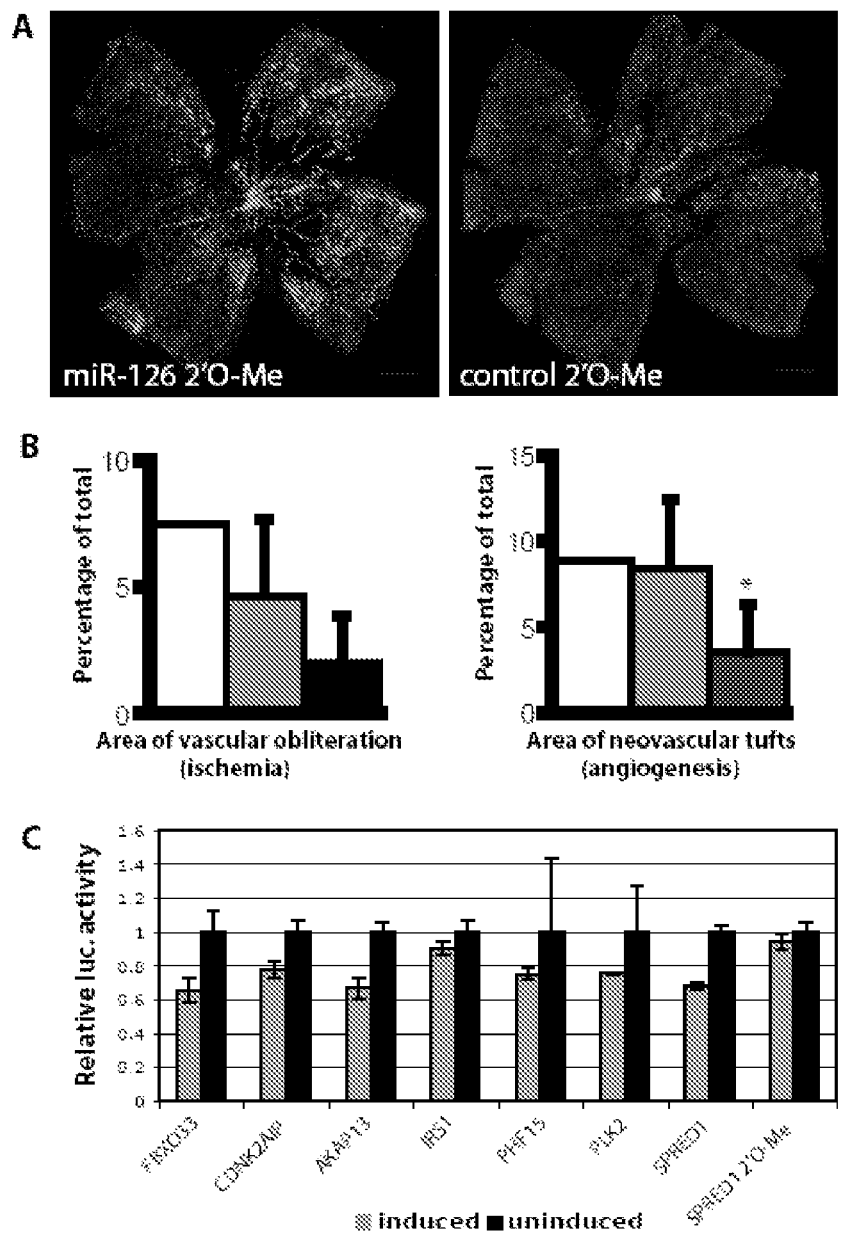
FIG. 6. miR-126. Inhibition of miR-126 prevents the formation of neo-vascular tufts in ischemic induced retinopathy of prematurity. C57/BL6/129S mice received an intravitreal injection of anti miR-126 2'O-Me in one eye and control 2'-O-Me in the other eye on P12 after undergoing oxygen-induced retinopathy. Retinas were examined by whole-mount microscopy. Inhibition of miR-126 by the antisense 2'-O-Me oligoribonucleotide decreases vascularization. (A) Representative images of retinal vasculature stained with isolectin B4-FITC showing vaso-obliteration and neovascularization (scale bar, 1 mm) (B) Quantification of vascular obliteration and angiogenic tufts from injections in 6 mice. *P less than or equal to 0.005. (C) Relative luciferase activity of constructs containing the 3' UTR of miR-126 predicted mRNA targets in HEK293 cells expressing inducible miR-126 in the presence (induced) or absence (uninduced) of miR-126/For each 3' UTR construct the levels of luciferase for uninduced cells was set to 1.

Results and Discussion miR-126 Knock Down in Zebrafish Embryos Impairs the Formation of Functional Stabilized Neovessels We studied the function of miR-126 in vivo using zebrafish as a model organism. We used transgenic Tg(fli1:EGFP)y1 zebrafish expressing GFP under the vascular-specific fli1 promoter, facilitating the observation of the vascular system. We inhibited miR-126 using morpholinos antisense to the miRNA. Morpholinos (MO) have been used extensively in zebrafish for the inhibition of mRNA translation and splicing. More recently they have also been applied to block miR-NAs9-11. Embryos were injected with an anti miR-126 MO at the one to two cell-stage and analyzed 24 and 48 h post-fertilization (hpf). The phenotypic penetrance of miR-126 MOs was dose-dependent. At 10 ng most embryos had a relatively normal morphology. However, at 15 ng, 74.5±10.2% of embryos manifested "angiogenic phenotypes" with shorter intersegmental vessels and a branching defect (FIG. 6C). To investigate whether miR-126 interacts genetically with VEGF-A, we co-injected anti-miR-126 MO (5 ng)+VEGF MO at doses that would not result in an angiogenic phenotype when injected independently (7.5 ng and 0.5 ng respectively). The combination resulted in an angiogenic phenotype that resulted in a more pronounced phenotype than the high dose of miR-126 MO by itself (FIGS. 5B & C). The development of intersegmental vessels was perturbed with defective or total absence of sprouting as well as absence of blood flow through these vessels through the time of observation (until 72 hpf).

Angiogenesis Suppression by miR-126 Inhibition in the Mouse Retina

Inhibition of miRNA function by antisense oligonucleotides has also been employed in mammals (12,13). Many studies describe the in vivo administration of naked siRNAs formulated in saline, with or without modifications, directly into a variety of tissues (reviewed in (14)). Intravitreal injection of VEGF-A or VEGF receptor targeting siRNAs successfully reduced neovascularization in two mouse models of eye disease (15). However, there is now debate whether double stranded anti VEGF-A siRNA, currently in clinical trial to inhibit choroidal neovascularization, functions solely through its intended target (16). Single stranded RNAs, such as miR-126 inhibitors, may therefore serve as an attractive therapeutic alternative.

Ocular neovascularization is modeled in the mouse with oxygen-induced vessel loss, which triggers hypoxia-induced anomalous vascularization allowing for assessment of retinal vessel loss, vessel regrowth after injury and pathological angiogenesis (17). Inhibition of miR-126 by antisense 2'-O-methyl oligoribonucleotides (2'O-Me) resulted in a significant decrease of vascular tufts and also in a reduction of the vascular obliterated area, compared to control 2'O-Me injections (FIGS. 6A & B). Antisense oligonucleotides linked to a cholesterol group have been shown to permeate the cells when administered systemically (12). We also tested miR-126 inhibitors with such chemical modifications, and found similar results. The oxygen-induced retinopathy model mimics ischemic disease that occurs in diabetic retinopathy and ROP. Therefore, our results have direct clinical implications for pathologic ocular neovascularization. In addition, recent evidence suggests that miR-126 does not directly inhibit VEGF-A or the VEGF receptor pathway (5). Thus, miR-126 inhibitory oligonucleotides are attractive for use as a sole therapeutic reagent or possibly for use in combination with current VEGF-A antibodies.

In Vitro Target Validation of Putative MiR-126 Targets

TargetScan computational miRNA target predictions were used to identify candidate miR-126 mRNA targets. For validation of these potential targets we used a standard dual luciferase assay (18). (see materials and methods). These assays were carried out in HEK293 cells expressing inducible miR-126. Reporter constructs were transfected into miR-126 positive and negative cells, and luciferase activities were measured. Five of the selected 3'UTRs showed down-regulation of the Renilla luciferase in cells expressing miR-126

(FIG. 6C). Several of these targets are related to cellular survival such as CDKN2AIP (CARF) a p53 stabilizing gene (19), PLK220, insulin receptor substrate 1 (IRS1) (21,22). Notably, the putative target SPRED1 was implicated to be involved in vascular endothelium development. SPRED1 suppresses lymphatic endothelial cell proliferation by negatively regulating VEGF-C23. It would be instructive to assess miR-126 expression in lymphatic endothelium and consider the possibility of miR-126 as a specific marker for vascular endothelium. In addition, SPRED1 was shown to inhibit cell motility and metastasis via the mitogen-activated protein kinase pathway (MAPK) (24) and furthermore to regulate the proliferation of hematopoietic cells via the ERK pathway (25).

REFERENCES FOR EXAMPLE 2

1. Poliseno L, Tuccoli A, Mariani L, et al. MicroRNAs modulate the angiogenic properties of HUVECs. Blood. 2006; 108:3068-3071.
2. Chen Y, Gorski D H. Regulation of angiogenesis through a microRNA (miR-130a) that down-regulates antiangiogenic homeobox genes GAX and HOXA5. Blood. 2008; 111:1217-1226.
3. Urbich C, Kuehbacher A, Dimmeler S. Role of microRNAs in vascular diseases, inflammation, and angiogenesis. Cardiovasc Res. 2008.
4. Wang S, Aurora A B, Johnson B A, et al. The endothelial-specific microRNA miR-126 governs vascular integrity and angiogenesis. Dev Cell. 2008; 15:261-271.
5. Fish J E, Santoro M M, Morton S U, et al. miR-126 regulates angiogenic signaling and vascular integrity. Dev Cell. 2008; 15:272-284.
6. Kuhnert F, Mancuso M R, Hampton J, et al. Attribution of vascular phenotypes of the murine Egfl7 locus to the microRNA miR-126. Development. 2008.
7. Banin E, Dorrell M I, Aguilar E, et al. T2-TrpRS inhibits preretinal neovascularization and enhances physiological vascular regrowth in OIR as assessed by a new method of quantification. Invest Ophthalmol V is Sci. 2006; 47:2125-2134.
8. Nasevicius A, Larson J, Ekker S C. Distinct requirements for zebrafish angiogenesis revealed by a VEGF-A morphant. Yeast. 2000; 17:294-301.
9. Flynt A S, Li N, Thatcher E J, Solnica-Krezel L, Patton J G. Zebrafish miR-214 modulates Hedgehog signaling to specify muscle cell fate. Nat. Genet. 2007; 39:259-263.
10. Kloosterman W P, Lagendijk A K, Ketting R F, Moulton J D, Plasterk R H. Targeted inhibition of miRNA maturation with morpholinos reveals a role for miR-375 in pancreatic islet development. PLoS Biol. 2007; 5:e203.
11. Woltering J M, Durston A J. MiR-10 represses HoxB1a and HoxB3a in zebrafish. PLoS ONE. 2008; 3:e1396.
12. Krutzfeldt J, Rajewsky N, Braich R, et al. Silencing of microRNAs in vivo with 'antagomirs'. Nature. 2005; 438:685-689.
13. de Fougerolles A, Vornlocher H P, Maraganore J, Lieberman J. Interfering with disease: a progress report on siRNA-based therapeutics. Nat Rev Drug Discov. 2007; 6:443-453.
14. de Fougerolles A R. Delivery vehicles for small interfering RNA in vivo. Hum Gene Ther. 2008; 19:125-132.
15. Shen J, Samul R, Silva R L, et al. Suppression of ocular neovascularization with siRNA targeting VEGF receptor 1. Gene Ther. 2006; 13:225-234.
16. Kleinman M E, Yamada K, Takeda A, et al. Sequence- and target-independent angiogenesis suppression by siRNA via TLR3. Nature. 2008; 452:591-597.
17. Smith L E, Wesolowski E, McLellan A, et al. Oxygen-induced retinopathy in the mouse. Invest Ophthalmol V is Sci. 1994; 35:101-111.
18. Lewis B P, Burge C B, Bartel D P. Conserved seed pairing, often flanked by adenosines, indicates that thousands of human genes are microRNA targets. Cell. 2005; 120:15-20.
19. Hasan M K, Yaguchi T, Harada J I, Hirano T, Wadhwa R, Kaul S C. CARF (collaborator of ARF) interacts with HDM2: evidence for a novel regulatory feedback regulation of CARF-p53-HDM2-p21WAF1 pathway. Int J. Oncol. 2008; 32:663-671.
20. Matthew E M, Yen T J, Dicker D T, et al. Replication stress, defective S-phase checkpoint and increased death in Pkl2-deficient human cancer cells. Cell Cycle. 2007; 6:2571-2578.
21. Werner H, Le Roith D. The insulin-like growth factor-I receptor signaling pathways are important for tumorigenesis and inhibition of apoptosis. Crit. Rev Oncog. 1997; 8:71-92.
22. Niessen M, Jaschinski F, Item F, McNamara M P, Spinas G A, Trub T. Insulin receptor substrates 1 and 2 but not Shc can activate the insulin receptor independent of insulin and induce proliferation in CHO-IR cells. Exp Cell Res. 2007; 313:805-815.
23. Taniguchi K, Kohno R, Ayada T, et al. Spreds are essential for embryonic lymphangiogenesis by regulating vascular endothelial growth factor receptor 3 signaling. Mol Cell Biol. 2007; 27:4541-4550.
24. Miyoshi K, Wakioka T, Nishinakamura H, et al. The Sprouty-related protein, Spred, inhibits cell motility, metastasis, and Rho-mediated actin reorganization. Oncogene. 2004; 23:5567-5576.
25. Nonami A, Kato R, Taniguchi K, et al. Spred-1 negatively regulates interleukin-3-mediated ERK/mitogen-activated protein (MAP) kinase activation in hematopoietic cells. J Biol. Chem. 2004; 279:52543-52551.

What is claimed is:

1. A method of inhibiting angiogenesis in a subject in need thereof, the method comprising administering to the subject an effective amount of an inhibitor of miR-126, wherein miR-126 is set forth in SEQ ID. NO: 1 or SEQ ID. NO: 2.

2. The method of claim 1, wherein the subject has a condition selected from the group consisting of ocular neo-vascularization, retinopathy of prematurity, diabetic retinopathy, retinal vein occlusion, age-related macular degeneration, posterior uveitis, pathologic myopia, choroidal arteriosclerosis, rheumatoid arthritis, psoriasis, and cancer.

3. The method of claim 1, wherein the subject is a mammal.

4. The method of claim 1, wherein the subject is a human.

5. The method of claim 1, wherein the inhibitor of miR-126 is a nucleic acid-based inhibitor.

6. The method of claim 5, wherein the nucleic acid-based inhibitor is an antisense oligonucleotide.

7. The method of claim 6, wherein the antisense oligonucleotide comprises ribonucleotides, deoxyribonucleotides, 2'-modified nucleotides, phosphorothioate linked deoxyribonucleotides, peptide nucleic acids (PNAs), or locked nucleic acids (LNAs).

8. The method of claim 6, wherein the antisense oligonucleotide comprises morpholinos or antagomirs.

9. The method of claim 5, wherein the nucleic acid-based inhibitor of miR-126 comprises a nucleotide sequence that forms a duplex with miR-126.

10. The method of claim 5, wherein the nucleic acid-based inhibitor of miR-126 comprises a nucleotide sequence selected from the group consisting of: SEQ ID. NO. 4, SEQ ID. NO. 5, and SEQ ID. NO. 6.

11. A method of treating an eye disease associated with excessive blood vessel growth in a subject in need thereof, the method comprising administering to the subject an effective amount of an inhibitor of miR-126, wherein miR-126 is set forth in SEQ ID. NO: 1 or SEQ ID. NO: 2.

12. The method of claim 11, wherein the eye disease is selected from the group consisting of ocular neo-vascularization, retinopathy of prematurity, diabetic retinopathy, retinal vein occlusion, age-related macular degeneration, posterior uveitis, pathologic myopia, and choroidal arteriosclerosis.

13. The method of claim 11, wherein the subject is a mammal.

14. The method of claim 11, wherein the subject is a human.

15. The method of claim 11, wherein the inhibitor of miR-126 is a nucleic acid-based inhibitor.

16. The method of claim 15, wherein the nucleic acid-based inhibitor is an antisense oligonucleotide.

17. The method of claim 16, wherein the antisense oligonucleotide comprises ribonucleotides, deoxyribonucleotides, 2'-modified nucleotides, phosphorothioate linked deoxyribonucleotides, peptide nucleic acids (PNAs), or locked nucleic acids (LNAs).

18. The method of claim 16, wherein the antisense oligonucleotide comprises morpholinos or antagomirs.

19. The method of claim 15, wherein the nucleic acid-based inhibitor of miR-126 comprises a nucleotide sequence that forms a duplex with miR-126.

20. The method of claim 15, wherein the nucleic acid-based inhibitor of miR-126 comprises a nucleotide sequence selected from the group consisting of: SEQ ID. NO. 4, SEQ ID. NO. 5, and SEQ ID. NO. 6.

21. The method of claim 11, wherein the inhibitor is administered intraocularly.

22. The method of claim 5 or 9, wherein said nucleic acid-based inhibitor of miR-126 is at least 19 nucleotides in length.

23. The method of claim 11 or 19, wherein said nucleic acid-based inhibitor of miR-126 is at least 19 nucleotides in length.

\* \* \* \* \*

```
                         SEQUENCE LISTING

<160> NUMBER OF SEQ ID NOS: 38

<210> SEQ ID NO 1
<211> LENGTH: 21
<212> TYPE: RNA
<213> ORGANISM: Unknown
<220> FEATURE:
<223> OTHER INFORMATION: Description of Unknown: MiR-126 oligonucleotide

<400> SEQUENCE: 1
```
ucguaccgug aguaauaaug c                                              21

<210> SEQ ID NO 2
<211> LENGTH: 22
<212> TYPE: RNA
<213> ORGANISM: Unknown
<220> FEATURE:
<223> OTHER INFORMATION: Description of Unknown: MiR-126 oligonucleotide

<400> SEQUENCE: 2
ucguaccgug aguaauaaug cg                                             22

<210> SEQ ID NO 3
<211> LENGTH: 85
<212> TYPE: RNA
<213> ORGANISM: Unknown
<220> FEATURE:
<223> OTHER INFORMATION: Description of Unknown: MiR-126 precursor
      oligonucleotide

<400> SEQUENCE: 3
cgcuggcgac gggacauuau uacuuuuggu acgcgcugug acacuucaaa cucguaccgu     60
gaguaauaau gcgccgucca cggca                                          85

<210> SEQ ID NO 4
<211> LENGTH: 21
<212> TYPE: RNA
<213> ORGANISM: Unknown
<220> FEATURE:
<223> OTHER INFORMATION: Description of Unknown: MiR-126 inhibitor
      oligonucleotide

<400> SEQUENCE: 4
gcauuauuac ucacgguacg a                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl-guanine
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (2)..(2)
<223> OTHER INFORMATION: 2'-O-Methyl-cytosine
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: modified_base
<222> LOCATION: (3)..(3)
<223> OTHER INFORMATION: 2'-O-Methyl-adenine
<220> FEATURE:
<221> NAME/KEY: modified_base
<222> LOCATION: (4)..(5)
<223> OTHER INFORMATION: 2'-O-Methyl-uracil
<220> FEATURE:
<221> NAME/KEY: modified_base
<222> LOCATION: (6)..(6)
<223> OTHER INFORMATION: 2'-O-Methyl-adenine
<220> FEATURE:

-continued

```
<221> NAME/KEY: modified_base
<222> LOCATION: (7)..(8)
<223> OTHER INFORMATION: 2'-O-Methyl-uracil
<220> FEATURE:
<221> NAME/KEY: modified_base
<222> LOCATION: (9)..(9)
<223> OTHER INFORMATION: 2'-O-Methyl-adenine
<220> FEATURE:
<221> NAME/KEY: modified_base
<222> LOCATION: (10)..(10)
<223> OTHER INFORMATION: 2'-O-Methyl-cytosine
<220> FEATURE:
<221> NAME/KEY: modified_base
<222> LOCATION: (11)..(11)
<223> OTHER INFORMATION: 2'-O-Methyl-uracil
<220> FEATURE:
<221> NAME/KEY: modified_base
<222> LOCATION: (12)..(12)
<223> OTHER INFORMATION: 2'-O-Methyl-cytosine
<220> FEATURE:
<221> NAME/KEY: modified_base
<222> LOCATION: (13)..(13)
<223> OTHER INFORMATION: 2'-O-Methyl-adenine
<220> FEATURE:
<221> NAME/KEY: modified_base
<222> LOCATION: (14)..(14)
<223> OTHER INFORMATION: 2'-O-Methyl-cytosine
<220> FEATURE:
<221> NAME/KEY: modified_base
<222> LOCATION: (15)..(16)
<223> OTHER INFORMATION: 2'-O-Methyl-guanine
<220> FEATURE:
<221> NAME/KEY: modified_base
<222> LOCATION: (17)..(17)
<223> OTHER INFORMATION: 2'-O-Methyl-uracil
<220> FEATURE:
<221> NAME/KEY: modified_base
<222> LOCATION: (18)..(18)
<223> OTHER INFORMATION: 2'-O-Methyl-adenine
<220> FEATURE:
<221> NAME/KEY: modified_base
<222> LOCATION: (19)..(19)
<223> OTHER INFORMATION: 2'-O-Methyl-cytosine
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: modified_base
<222> LOCATION: (20)..(20)
<223> OTHER INFORMATION: 2'-O-Methyl-guanine
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (21)..(21)
<223> OTHER INFORMATION: 2'-O-Methyl-adenine with cholesterol linked
      through a hydroxyprolinol linkage

<400> SEQUENCE: 5
gcauuauuac ucacgguacg a                                              21

<210> SEQ ID NO 6
<211> LENGTH: 22
<212> TYPE: RNA
<213> ORGANISM: Unknown
<220> FEATURE:
<223> OTHER INFORMATION: Description of Unknown: MiR-126 inhibitor
      oligonucleotide

<400> SEQUENCE: 6
cgcauuauua cucacgguac ga                                             22
```

```
<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgcattatta ctcacggtac ga                                              22

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtatcaaata aacaaccaag ttcat                                           25

<210> SEQ ID NO 9
<211> LENGTH: 16
<212> TYPE: PRT
<213> ORGANISM: Drosophila sp.

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 14
<212> TYPE: PRT
<213> ORGANISM: Human immunodeficiency virus

<400> SEQUENCE: 10

Gly Arg Lys Lys Arg Arg Gln Arg Arg Pro Pro Gln Cys
1               5                   10

<210> SEQ ID NO 11
<211> LENGTH: 27
<212> TYPE: PRT
<213> ORGANISM: Unknown
<220> FEATURE:
<223> OTHER INFORMATION: Description of Unknown: Signal sequence based
      peptide

<400> SEQUENCE: 11

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 12
<211> LENGTH: 18
<212> TYPE: PRT
<213> ORGANISM: Unknown
<220> FEATURE:
<223> OTHER INFORMATION: Description of Unknown: PVEC peptide

<400> SEQUENCE: 12

Leu Leu Ile Ile Leu Arg Arg Arg Ile Arg Lys Gln Ala His Ala His
1               5                   10                  15

Ser Lys
```

<210> SEQ ID NO 13
<211> LENGTH: 26
<212> TYPE: PRT
<213> ORGANISM: Unknown
<220> FEATURE:
<223> OTHER INFORMATION: Description of Unknown: Transportan peptide

<400> SEQUENCE: 13

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 14
<211> LENGTH: 18
<212> TYPE: PRT
<213> ORGANISM: Unknown
<220> FEATURE:
<223> OTHER INFORMATION: Description of Unknown: Amphiphilic model
      peptide

<400> SEQUENCE: 14

Lys Leu Ala Leu Lys Leu Ala Leu Lys Ala Leu Lys Ala Ala Leu Lys
1               5                   10                  15

Leu Ala

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Arg Arg Arg Arg Arg Arg Arg
1               5

<210> SEQ ID NO 16
<211> LENGTH: 31
<212> TYPE: PRT
<213> ORGANISM: Unknown
<220> FEATURE:
<223> OTHER INFORMATION: Description of Unknown: Cecropin P1 peptide

<400> SEQUENCE: 16

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 17
<211> LENGTH: 30
<212> TYPE: PRT
<213> ORGANISM: Homo sapiens

<400> SEQUENCE: 17

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 18
<211> LENGTH: 36

<212> TYPE: PRT
<213> ORGANISM: Homo sapiens

<400> SEQUENCE: 18

```
Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35
```

<210> SEQ ID NO 19
<211> LENGTH: 12
<212> TYPE: PRT
<213> ORGANISM: Unknown
<220> FEATURE:
<223> OTHER INFORMATION: Description of Unknown: Bactenecin peptide

<400> SEQUENCE: 19

```
Arg Lys Cys Arg Ile Val Val Ile Arg Val Cys Arg
1               5                   10
```

<210> SEQ ID NO 20
<211> LENGTH: 42
<212> TYPE: PRT
<213> ORGANISM: Unknown
<220> FEATURE:
<223> OTHER INFORMATION: Description of Unknown: PR-39 peptide
<220> FEATURE:
<223> OTHER INFORMATION: C-term amidated

<400> SEQUENCE: 20

```
Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40
```

<210> SEQ ID NO 21
<211> LENGTH: 13
<212> TYPE: PRT
<213> ORGANISM: Unknown
<220> FEATURE:
<223> OTHER INFORMATION: Description of Unknown: Indolicidin peptide
<220> FEATURE:
<223> OTHER INFORMATION: C-term amidated

<400> SEQUENCE: 21

```
Ile Leu Pro Trp Lys Trp Pro Trp Trp Pro Trp Arg Arg
1               5                   10
```

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Ala Ala Val Ala Leu Leu Pro Ala Val Leu Leu Ala Leu Leu Ala Pro
1               5                   10                  15
```

<210> SEQ ID NO 23

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Leu Leu Pro Val Leu Leu Ala Ala Pro
1               5                   10

<210> SEQ ID NO 24
<211> LENGTH: 13
<212> TYPE: PRT
<213> ORGANISM: Human immunodeficiency virus

<400> SEQUENCE: 24

Gly Arg Lys Lys Arg Arg Gln Arg Arg Arg Pro Pro Gln
1               5                   10

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccctagcaac aagtcactgg a                                          21

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgtgtccaaa atatcactgc atacaa                                     26

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acagaaccgc ttaccaagaa ctg                                        23

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggtacgatg catccatttc                                            20

<210> SEQ ID NO 29
<211> LENGTH: 21
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 29
ggtcacttcc accactggta a                                          21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30 atggaccta tgggactcct                                             20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
aatggtccag tgccaaaatg                                            20

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tttaacacta aaagtagtca tgcttca                                    27

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gaaaattgaa gggaatcgct ttt                                        23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ctggatcaag ttctggcctc taa                                        23

<210> SEQ ID NO 35
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 35
atggtgggaa tagagcagga                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caagtgctga gactgctgga                                                   20

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttttcatact ctttattgcc aacg                                              24

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acggcaaaat cttagcagca                                                   20
```